United States Patent
Flint et al.

(10) Patent No.: US 6,239,072 B1
(45) Date of Patent: May 29, 2001

(54) TANK MIXTURES AND PREMIXTURES FOR WEED CONTROL PROGRAMS THAT INCLUDE POSTMERGENCE APPLICATIONS OF GLYPHOSATE PLUS GRAMINICIDES IN GLYPHOSATE TOLERANT SOYBEANS

(75) Inventors: Jerry L. Flint; Norman J. Probst, both of Chesterfield; Nagabhushana G. Gubbiga, Hazelwood, all of MO (US)

(73) Assignee: Monsanto Company, St. Louis, MO (US)

(*) Notice: Subject to any disclaimer, the term of this patent is extended or adjusted under 35 U.S.C. 154(b) by 0 days.

(21) Appl. No.: 09/264,775

(22) Filed: Mar. 9, 1999

Related U.S. Application Data
(60) Provisional application No. 60/077,241, filed on Mar. 9, 1998.

(51) Int. Cl.[7] .................... A01N 35/06; A01N 43/40; A01N 43/54; A01N 43/76; A01N 57/02
(52) U.S. Cl. .................................. 504/127; 504/128
(58) Field of Search .................................. 504/127, 128

(56) References Cited

U.S. PATENT DOCUMENTS

| | | | |
|---|---|---|---|
| 3,799,758 | 3/1974 | Franz | 71/86 |
| 3,927,080 | 12/1975 | Gaertner | 260/502.5 |
| 3,956,370 | 5/1976 | Parry et al. | 260/502.5 |
| 3,969,398 | 7/1976 | Hershman | 260/502.5 |
| 4,147,719 | 4/1979 | Franz | 260/501.12 |
| 4,654,429 | 3/1987 | Balthazor et al. | 558/145 |
| 5,310,667 | 5/1994 | Eichholtz et al. | 435/172.3 |
| 5,312,910 | 5/1994 | Kishore et al. | 536/23.2 |
| 5,463,175 | 10/1995 | Barry et al. | 800/205 |

FOREIGN PATENT DOCUMENTS

| | | | |
|---|---|---|---|
| 0 144 137 | * 6/1985 | (EP) | A01N/57/20 |
| 0 808 569 | 11/1997 | (EP) | |
| 2 233 229 | * 1/1991 | (GB) | A01N/57/20 |
| WO 99 13723 | 3/1999 | (WO) | |
| WO 00 35287 | 6/2000 | (WO) | |

OTHER PUBLICATIONS

Database CROPU Online! DerWent Information Ltd Lueschen W et al.: "Postermrgence herbicides for volunteer corn control in soybean" Database accession No. 93–87767 XP002109572 abstract & Res. Rep. North Cent. Weed Sci. Soc., vol. 49, 1992, pp. 323–324.

MN Agric. Exp. Stn. Pater No. 20098, Misc. Journ. Series, University of NM, St. Paul "Weed Control In Reduced Tillage and Chemical Fallow—Soybean" No Date.

Flint, Jerry L. et al. (1989) "Antagonism of Glyphosate Toxicity to Johnsongrass (*Sorghum halepense*) by 2,4–D and Dicamba," *Weed Science* 37:700–705.

Lich, Julie M. et al. (1997) "Interaction of glyphosate with postemergence soybean (*Glycine max*) herbicides," *Weed Science* 45:12–21.

Young, Brian G. et al. (1997) "Control of Volunteer Sethoxydim–Resistant Corn (*Zea mays*) in Soybean (*Glycine max*)," *Weed Technology* 11:649–655.

* cited by examiner

*Primary Examiner*—S. Mark Clardy
(74) *Attorney, Agent, or Firm*—Howrey Simon Arnold & White, LLP; Jon Beusen

(57) ABSTRACT

The present invention is directed to tank mixtures and premixtures of a glyphosate herbicide and a second herbicide to which a first species is susceptible and a second species is resistant. Such tank mixtures and premixtures allow control of glyphosate-susceptible weeds and glyphosate-tolerant volunteer individuals of the first species in a crop of glyphosate-tolerant second species with a single application of herbicide.

21 Claims, 1 Drawing Sheet

Fig. 1

TANK MIXTURES AND PREMIXTURES FOR WEED CONTROL PROGRAMS THAT INCLUDE POSTMERGENCE APPLICATIONS OF GLYPHOSATE PLUS GRAMINICIDES IN GLYPHOSATE TOLERANT SOYBEANS

This application claims the benefit of U.S. provisional application Serial No. 60/077,241, filed Mar. 9, 1998.

BACKGROUND OF THE INVENTION

1. Field of the Invention

The present invention relates generally to the field of weed control in crop plants. More particularly, it concerns the control of volunteer plants expressing a gene imparting glyphosate tolerance in a field of a glyphosate-tolerant crop species by use of tank mixtures or premixtures of a glyphosate herbicide with a second herbicide with a different mode of action, activity against the volunteer plant species, and lack of activity against the crop species. Most particularly, it relates to the control of volunteer glyphosate-tolerant corn in a crop of glyphosate-tolerant soybean by use of tank mixtures or premixtures of a glyphosate herbicide with a graminicide such as sethoxydim, clethodim, quizalofop, fluazifop, fenoxaprop, imazamox, imazethapyr, and imazaquin.

2. Description of Related Art

Chemical agents to inhibit plant metabolism have been widely used since the 1940's. One popular herbicide is glyphosate (N-phosphonomethylglycine; trade name ROUNDUP®). When applied, glyphosate is taken up by plants and subsequently inhibits 5-enolpyruvylshikimate-3-phosphate synthase (EPSPS). Inhibition of EPSPS blocks the formation of aromatic amino acids which are required components of plant hormones and vitamins. The plants in the field die after exposure to glyphosate, and any residual glyphosate in the soil is rapidly broken down. A limitation is that glyphosate may not be applied after planting of a crop, because glyphosate will cause crop injury.

By use of recombinant DNA technology, crop plants such as soybean, corn, cotton, wheat, canola, sugarbeet, rice, and lettuce, among others, have been developed with EPSPS resistant to inhibition by glyphosate. As a result, growers may use glyphosate to control weeds throughout the growing season of a glyphosate-tolerant crop without injuring crop plants.

A limitation on this technique is the presence of glyphosate-tolerant plants that are not members of the crop species. No uncultivated species of weed has been observed to naturally develop glyphosate-tolerance, and the flow of genes for glyphosate tolerance from crop plants to related wild species is not expected to occur. Rather, the expected source of glyphosate-tolerant plants that are not members of the crop species is the species planted in a given field the previous growing season. For example, in many parts of the Midwestern U.S., farmers alternate crops of corn and soybean in alternate years, a practice known as crop rotation. If kernels from the ears or whole ears of corn fall to the ground, either naturally or the result of insect damage or harvesting loss, then the fertilized kernels may lie dormant over the winter and germinate during the following growing season. Corn plants growing in a crop of soybeans, the corn plants being the progeny of a crop of corn grown in that field the previous growing season, are called volunteer corn plants. More generally, volunteer plants of any species may grow in situations in which farmers practice crop rotation between any two species.

Volunteer plants are as undesirable as undomesticated weeds, in that both grow by absorbing sunlight, soil nutrients, and soil moisture that the farmer prefers be absorbed by the crop species. Previously, volunteer plants, like weeds, could be controlled by application of a broad spectrum herbicide such as glyphosate. However, when the volunteer plants are progeny of a glyphosate-tolerant crop, the application of glyphosate to the field will control undomesticated weed species, but not the volunteer plant species. Given the wide adoption of glyphosate-tolerant species, and the practice of crop rotation, a need exists for a method for controlling glyphosate-tolerant volunteer plant species growing in a field of a glyphosate-tolerant crop species.

Therefore, a method to allow convenient control of both glyphosate-tolerant volunteer plant species and glyphosate-susceptible weeds by a single application is desirable. It is also desirable for such a method to control volunteer plants and weeds without injury to or yield loss in the crop species.

SUMMARY OF THE INVENTION

In one embodiment, the present invention is directed to tank mixtures and premixtures of a glyphosate herbicide with at least one other non-glyphosate herbicide.

In another embodiment, the present invention is directed to a method of controlling a volunteer species in a field of a crop species, comprising applying at least two herbicides in any order or simultaneously, wherein the volunteer species is controlled by at least one of the herbicides and the crop species is tolerant to all of the herbicides.

Preferably, the method uses a glyphosate herbicide and a non-glyphosate herbicide for control of both glyphosate-susceptible weeds and plants of glyphosate-tolerant volunteer species in a field of a glyphosate-tolerant crop species. The non-glyphosate herbicide is one that controls the glyphosate-tolerant volunteer species and is non-toxic to the glyphosate-tolerant crop species.

More preferably, the non-glyphosate herbicide is an ACCase inhibitor or an AHAS inhibitor, the glyphosate-tolerant volunteer species is corn, and the glyphosate-tolerant crop species is soybean, canola, sugarbeet, or cotton. Exemplary non-glyphosate herbicides include, but are not limited to, sethoxydim, clethodim, quizalofop, fluazifop, fenoxaprop, and imazamox.

DESCRIPTION OF ILLUSTRATIVE EMBODIMENTS

In one embodiment, the present invention is directed to tank mixtures and premixtures of a glyphosate herbicide with a non-glyphosate herbicide. Tank mixtures and premixtures can be generically termed "mixtures." These mixtures are especially useful in a method of controlling both glyphosate-susceptible weeds and a glyphosate-tolerant volunteer plant species in a field of a glyphosate-tolerant crop of a different plant species. The non-glyphosate herbicide is one to which plants of the volunteer species are susceptible, but to which plants of the different, crop species are tolerant.

Glyphosate has been known to be an effective broad spectrum herbicide for many years. Various methods are known for producing glyphosate, as shown in U.S. Pat. Nos. 3,927,080; 3,956,370; 3,969,398; 4,147,719; and 4,654,429. As used herein, "glyphosate" refers to N-phosphonomethylglycine, a salt or ester thereof, or a compound which is converted to glyphosate in plant tissues or which otherwise provides glyphosate ion. This includes the TMS salt of glyphosate (commercially available under the trade name TOUCHDOWN®, as well as sulfosate and its salts. Illustratively, glyphosate and its salts useful herein are disclosed in U.S. Pat. No. 3,799,758. It will be understood by one skilled in the art that many derivatives of N-phosphonomethylglycine will exhibit broad spectrum herbicidal activity, and thus any such herbicidal derivatives will be defined as glyphosate for the purposes of the present invention. Also, although most herbicidal formulations of glyphosate comprise salts of the anionic form of glyphosate in aqueous solution, any formulation of glyphosate is considered to be within the scope of the present invention. Further, any use of surfactants, wetting agents, or other agents for the purpose of enhancing the activity of glyphosate is deemed to be within the scope of the present invention.

Glyphosate tolerance may be imparted to plant species by recombinant DNA techniques that are described in the art (as described by U.S. Pat. Nos. 5,312,910; 5,310,667; 5,463,175.). Glyphosate tolerance is brought about by inserting either a gene encoding a modified 5-enolpyruvylshikimate-3-phosphate synthase (EPSPS) enzyme, a gene encoding a glyphosate oxidoreductase (Gox) enzyme, or both into the genome of a plant. Modified EPSPS imparts glyphosate tolerance by being less inhibited by glyphosate than is native plant EPSPS. The source of the gene encoding modified EPSPS may be a bacterial strain that has naturally developed a modified EPSPS tolerant to glyphosate, a synthesized double-stranded deoxyribonucleic acid designed to encode a modified EPSPS, or any other source. Gox imparts glyphosate tolerance by catalyzing the conversion of glyphosate to non-toxic compounds. The source of the gene encoding Gox may be a bacterial strain that naturally expresses Gox, a synthesized double-stranded deoxyribonucleic acid designed to encode Gox, or any other source.

Once genes encoding modified EPSPS or Gox are isolated, further modifications of the genes may optionally be made to increase or decrease the activity of the encoded enzyme, to enhance the expression of the gene, or for other reasons that may alter but not abolish the activity of the modified EPSPS or Gox enzyme. After the genes have been resolved into their desired final form, they may be inserted into the genome of a plant cell by any appropriate known technique of plant transformation, including, but not limited to, Agrobacterium infection, plant viral vector infection, electroporation, PEG-mediated transformation, and particle bombardment. Transformed plant cells, i.e. plant cells with a foreign gene inserted into their genome, may then be regenerated by well-known methods to produce fertile adult plants expressing the gene imparting glyphosate tolerance.

To date, lines of corn, cotton, soybean, sugarbeet, rice, wheat, canola, and lettuce, among others, that express a gene imparting glyphosate tolerance have been or are being commercialized. Production of lines of other plant species expressing a glyphosate-tolerance gene may be produced by techniques known in the art. See, e.g. U.S. Pat. Nos. 5,312,910; 5,310,667; 5,463,175. Therefore, the scope of the present invention reasonably covers the presently-known glyphosate-tolerant corn, cotton, soybean, wheat, canola, sugarbeet, rice, and lettuce, and any glyphosate-tolerant crop species that may be developed. Also, although the development of glyphosate-tolerant plants by use of conventional breeding without recombinant DNA techniques is currently believed to be highly unlikely, if any such naturally glyphosate-tolerant plants are developed they would fall within the scope of the current invention.

The non-glyphosate herbicide can be any herbicide to which the glyphosate-tolerant volunteer plant species is susceptible and to which the glyphosate-tolerant crop species is tolerant. One of ordinary skill in the art can readily determine an appropriate non-glyphosate herbicide for an intended purpose.

Exemplary non-glyphosate herbicides, and purposes for which they can be used, include, but are not limited to, primisulfuron or nicosulfuron for control of cotton, sorghum, peanut, rice, or soybean in corn; lactofen or oxyfluorfen for control of corn, sorghum, peanut, rice, or soybean in cotton; bromoxynil for control of cotton, peanut, rice, or soybean in sorghum; chlorimuron for control of corn, cotton, sorghum, or rice in peanut; bensulfuron for control of corn, cotton, sorghum, peanut, or soybean in rice; chlorimuron for control of corn, cotton, sorghum, or rice in soybean.

If corn is to be controlled in soybean or cotton, preferred non-glyphosate herbicides are acetyl coenzyme A carboxylase (ACCase) inhibitors or acetohydroxyacid synthase (AHAS) inhibitors. Examples of such preferred non-glyphosate herbicides include, but are not limited to, sethoxydim, clethodim, quizalofop, fluazifop, fenoxaprop, imazamox, imazethapyr, and imazaquin.

Mixtures of herbicides are also well-known in the art. Such mixtures can be tank mixtures, in which the end-user mixes two or more herbicides in the tank of the spraying apparatus, or premixtures, in which a supplier provides the end-user with a mixture of two or more herbicides in a known ratio.

A mixture of herbicides of the present invention may include various adjuvants. Surfactants are one such adjuvant. As is known, surfactants lower the surface tension of the spray, increasing spray coverage and penetration. Non-ionic surfactants (NIS) are usually used with herbicides. NIS may also contain fatty acids. Exemplary surfactants that can be used in the present invention include DASH®, a surfactant with fatty acids (BASF); FRIGATE®, a fatty amino ethoxylate (ISK Biosciences); and IMPROVE®, a fatty amine ethoxylate (DowElanco). DASH® can be used with the graminicide POAST®, whereas FRIGATE® and IMPROVE® can be used with ROUNDUP®. Nonionic surfactants (NIS) are typically polyoxyethylated aliphatic alcohols with a low percentage of siloxane to minimize foaming. Some also contain free fatty acids or fatty acid esters. The "active ingredient" often includes an alcohol solubilizer, which is not a "true" active ingredient. Most labels state that NIS should contain at least 80% active ingredient. NIS are typically used at 0.58–2.34 L/ha (0.5–2 pt/ac) or 0.125–0.5% by volume. Exemplary NIS that can be used in the present invention include ACTIVATE PLUS®, 90% active ingredient including free fatty acids or fatty acid ester (Terra Ind.); ACTIVATOR 90®, 85% active ingredient including free fatty acids or fatty acid ester (Loveland Ind.); ADDITIVE 80®, 80% active ingredient (Brower International); AD-SPRAY 80®, 80% active ingredient (Helena Chemical); AD-SPRAY 90®, 90% active ingredient (Helena Chemical); AGWAY SPREADER®, 80% active ingredient including free fatty acids or fatty acid ester (Agway Inc.); BIG SUR 90®, 90% active ingredient including free fatty acids or fatty acid ester (Brewer International); BIO-88®, 88% active ingredient including free fatty acids or fatty acid ester (Kalo, Inc.); BIOSURF®, 80% active ingredient (Platte Chemical); INDUCE®, 90% active ingredient including free fatty acids or fatty acid ester (Helena Chemical); LATRON AG-98®, 80% active ingredient (Rohrn and Haas); REGULAID®, 90% active ingredient (Kalo, Inc.); SATURALL 85®, 86% active ingredient including free fatty acids or fatty acid ester (Conklin); SPRAY FUSE 90®, 50% active ingredient including free fatty acids or fatty acid ester (Cornbelt Chemical); SPREADER 80®, 80% active ingredient (Custom Chemicides); STIK®, 90% active ingredient including free fatty acids or fatty acid ester (Custom Chemicides); SUPER SPRED®, 50% active ingredient (Wilbur Ellis); SURFAC 820®, 80% active ingredient (Drexel Chemical); SURFAC 910®, 90% active ingredient (Drexel Chemical); SURF-AID®, 80% active ingredient (Terra Ind.); UNIFILM 707®, 90% active ingredient including free fatty acids or fatty acid ester (Custom Chemicides); and X-77®, 90% active ingredient including free fatty acids or fatty acid ester (Loveland Ind.)

Other adjuvants known in the art which can be used in the present invention include crop oils, which contain phytobland (nonaromatic) paraffinic oils (mineral oil) of 70- to 110-second viscosity. They are also called dormant spray oils. Crop oils are 96%–98% oil and 1%–2% nonionic surfactant and are usually used at 9.36–18.72 L/ha (1–2 gal/ac, i.e. 4%–8% by volume). As is known in the art, "crop oil" is a misnomer, as it is mineral and not crop (vegetable) oil. Exemplary crop oils that can be used in the present invention include CROP OIL® (Combelt Chemical) and NP-99® (Farmbelt Chemical).

Further known adjuvants that can be used in the present invention include crop oil concentrates (COC), which are phytobland oils of petroleum origin [POC] or crop origin [COO] with surfactant (emulsifier) to allow them to be miscible with water. Oils increase the penetration of the spray through the cuticle (waxy layer) of the leaves. They contain 83%–85% oil and 15%–17% nonionic surfactant. They are used at about 1.17–3.51 L/ha (1–3 pt/ac), or about 1% volume/volume basis. As is known in the art, the term "oil concentrate" is a misnomer as COCs contain less oil than crop oils. Exemplary crop oil concentrates that can be used in the present invention include ACTIVATE OIL ADJUVANT® (Drexel Chemical); ADD-IT® (Agsco); ADJUMEC® (PBI/Gordon); AGRI-DEX® (fatty acid esters added; Helena Chemical); CROP OIL EXTRA® (Kalo, Inc.); INVADE PLUS® (Terra Ind.); PENETRATOR® (fatty acid esters added; Helena Chemical); PEPTOIL® (Drexel Chemical); PRIME OIL® (Terra Ind.); STA-RITE 120® (Precision Labs); SUPER SAVOL® (Uniroyal Chemical); and SURFEL® (Rhone-Poulenc).

Additional adjuvants known in the art that can be used in the present invention include crop origin oils (COO), sometimes called vegetable oil concentrates (VOC). COOs contain 85%–93% highly refined vegetable oil and 10%–15% surfactant. As is known in the art, some herbicide labels allow COO to replace COC, but some specify petroleum-based only. Exemplary crop origin oils that can be used in the present invention include ADD-IT-TO-OIL® (vegetable source; Drexel Chemical); LI 700® (soybean source; Loveland Ind.); NATUR'L OIL® (vegetable source; Stoller Chem.); PRIME OIL II® (vegetable source; Terra Ind.); SUN-IT® (sunflower source, methylated to form fatty acid esters; Agsco); SUN-IT II® (vegetable source, methylated to form fatty acid esters; Agsco); VEGETOIL® (vegetable source; Drexel Chemical); and VEG-OIL CONCENTRATE® (vegetable source; Helena Chemical).

Liquid fertilizers (28-0-0, 10-34-0) as adjuvants are also known in the art. Liquid fertilizers are commonly added to increase activity on velvetleaf. They are generally used with NIS or COC with contact herbicides and systemic herbicides. An exemplary liquid fertilizer is UAN, urea/ammonium nitrate (28% nitrogen).

Buffers are adjuvants used by those of skill in the art to maintain or reduce pH to prevent alkaline hydrolysis of some pesticides. They contain phosphatic acid esters plus free phosphatic acid (buffer and surfactant). Exemplary buffers that can be used in the current invention include BALANCE® (Precision Labs); BS-500® (Drexel Chemical); BUFFER P.S.® (Helena Chemical); BUFFER XTRA STRENGTH® (Helena Chemical); BUFFER-PLUS® (Custom Chemicides); BUFFER-X® (Kalo, Inc.); PENETRATOR PLUS® (Helena Chemical); SURPHACTANT PH® (Brewer International); and UNIFILM B® (Custom Chemicides).

Further adjuvants known in the art that can be used in the present invention include compatibility agents, which help maintain emulsion stability when herbicides are mixed and applied with liquid fertilizer solutions. Compatibility agents are usually phosphatic esters of alkyl aryl polyoxy (ethanol, ethylene glycol or ethylene ethers) with alcohol solubilizers (ethanol, methanol, or isopropanol). Compatibility agents may also contain extra phosphatic acids for buffering effects. The rate is typically 0.12%–0.5% volume/volume. The lower rate is typically used for nitrogen solutions such as UAN; the moderate rate is typically used for nitrogen/phosphorous solutions such as APP; and the higher rate is typically used for nitrogen/phosphorous/potassium solutions with solubilized KCl or $K_2SO_4$. Exemplary phosphate ester compatibility agents that can be used in the present invention include BLENDEX®, 64% active ingredient (Helena Chemical); COMBINE®, 95% active ingredient (Terra Ind.); and E-Z MIX®, 85% active ingredient (Loveland Ind.).

The relative advantage of tank mixtures vs. premixtures and/or the use of adjuvants depends on cost, flexibility, occupational safety, and other concerns. The primary advantage of mixtures over non-mixtures is convenience; two or more herbicides may be applied simultaneously to control a broader spectrum of weeds than may be controlled by either herbicide alone.

The present invention is also directed to a method using tank mixtures or premixtures comprising any two herbicides, in a method of controlling both weeds and a volunteer species in a field of a crop species, provided the volunteer species is controlled by at least one of the herbicides in the mixture, whereas the crop species is tolerant to both of the herbicides in the mixture.

The method will be described in detail concerning the use of both a glyphosate herbicide and a non-glyphosate herbicide. However, one of ordinary skill in the art will appreciate that the method can use any two herbicides as described above. For example, the method can make use of glufosinate plus sethoxydim to control glufosinate-tolerant volunteer corn present in glufosinate-tolerant soybeans, or glyphosate plus imazamox to control a segregating population of glyphosate tolerant and sethoxydim resistant volunteer corn in glyphosate tolerant soybeans.

The present invention is also directed to the use of both a glyphosate herbicide and a non-glyphosate herbicide in a method of controlling both glyphosate-susceptible weeds and a glyphosate-tolerant volunteer plant species in a field of a glyphosate-tolerant crop of a different plant species. The non-glyphosate herbicide must be one to which plants of the volunteer species are susceptible, but to which plants of the different, crop species are tolerant.

The glyphosate herbicide and the non-glyphosate herbicide can be applied simultaneously as a tank mixture or premixture, or can be applied separately, in either order. The relative advantages of different modes of application may depend on the volunteer and crop species, cost, occupational safety, environmental conditions, and other parameters. Determining the relative advantages is within the ordinary skill in the art. In general, however, separate application is less preferred because the primary advantage of a mixture, the convenience of only one application, is not realized.

Glyphosate-tolerant volunteer species that can be controlled in glyphosate-tolerant crop species include, but are not limited to, volunteer cotton, sorghum, peanut, rice, or soybean in a corn crop; volunteer corn, sorghum, peanut, rice, or soybean in a cotton crop; volunteer cotton, peanut, rice, or soybean in a sorghum crop; volunteer corn, cotton, sorghum, or rice in a peanut crop; volunteer corn, cotton, sorghum, peanut, or soybean in a rice crop; volunteer corn, wheat, soybean, or rice in a sugarbeet crop; volunteer corn, wheat, soybean, or rice in a canola crop; and volunteer corn, cotton, canola, sorghum, wheat, or rice in a soybean crop.

In one embodiment of the invention, the tolerance of plants of the crop species to the non-glyphosate herbicide, and the susceptibility of plants of the volunteer species to the non-glyphosate herbicide, are both natural features of the two species. One example of this embodiment is the different responses of corn and soybean to the non-glyphosate herbicides fluazifop, quizalofop, clethodim, sethoxydim, fexoxaprop, and imazamox, among others. As is well-known in the art, corn is controlled by the application of any one of the above non-glyphosate herbicides, but soybean is tolerant to all of the above. Therefore any of fluazifop, quizalofop, clethodim, sethoxydim, fenoxaprop, and imazamox, among others well-known in the art, may be used to control glyphosate-tolerant volunteer corn plants in a field of glyphosate-tolerant soybean.

In a second embodiment of the present invention, the tolerance of plants of the crop species to the non-glyphosate herbicide is imparted by inserting into the genome of plants of the crop species a gene encoding an enzyme which renders the plant resistant to the non-glyphosate herbicide. Plants of the volunteer species remain susceptible to the non-glyphosate herbicide. Production of tolerance to the non-glyphosate herbicide in the crop species is achieved by use of the techniques described above for production of glyphosate tolerance.

The method is useful with any of the pairs of volunteer and crop species given above, and others not disclosed but either well-known or easily determined without undue experimentation, provided glyphosate tolerance has been imparted as described above.

In the above embodiments, exhibition of glyphosate tolerance by the plants of the crop species is required. It is further anticipated that plants of the volunteer species exhibit glyphosate tolerance as well. However, if plants of the volunteer species do not exhibit glyphosate resistance, the application of mixtures of a glyphosate herbicide and a non-glyphosate herbicide which are the subject of the present invention should control them as effectively as glyphosate alone. For example, a situation may occur in which glufosinate-tolerant corn is present as a volunteer species in glyphosate-tolerant soybean.

One possible difficulty that may be posed to mixtures in embodiments of the present invention is antagonism between the glyphosate herbicide and the non-glyphosate herbicide, or between either herbicide and a surfactant or other inert ingredient. Antagonism is defined as a negative interaction between the components of a mixture of herbicides, which results in inferior control of target weeds relative to what would be expected from considering the activities of the component herbicides individually.

However, antagonism is unlikely in light of the present disclosure. Antagonism is generally limited to mixtures of herbicides or herbicides and surfactants in which the components target the same enzyme or the same metabolic pathway in the plant, or in which the components interfere with absorption into the plant. Such situations are well-known to those of skill in the art, and can be avoided by refraining from using antagonistic mixtures or improving absorption by addition of new and/or different surfactants and wetting agents to the mixtures or by use of different techniques of application to plants. Antagonism in glyphosate mixtures has been described by, among others, Flint et al., *Weed Science* (1989), 37, 700–705, and Lich et al., *Weed Science* (1997), 45, 12–21. Further data is provided in the Examples below, which demonstrate that mixtures of glyphosate and non-glyphosate herbicides can be used in the present method without concern for antagonism.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Trials were conducted at four sites in the Midwestern U.S. Multiple test plots were grown at each site. In each test plot, rows of glyphosate-tolerant soybeans and test corn were planted. Four corn lines were tested. The first, "Natalie," contained a glyphosate tolerance gene. The second, "Absurd," was bred to express a *Bacillus thuringiensis* crystal protein insecticidal gene, but also was believed to contain a glyphosate tolerance gene used as a selectable marker in breeding. The third contained a sethoxydim tolerance gene. The fourth was a native, non-herbicide-tolerant corn line. Also planted at each trial location were one species each of grass and broadleaf weeds to evaluate possible antagonism between the components of each mixture.

Eight mixtures were prepared for testing, as listed in Table 1:

TABLE 1

Herbicide formulations and rates of applications. ROUNDUP ULTRA ® was formulated at 0.84 kg of acid equivalent (kg AE)/ha, and all other herbicides were formulated using kg of active ingredient (kg AI)/ha.

| Treatment | Herbicide(s) | Rate (kg AE or AI/ha (lbs. AE or AI/acre)) |
|---|---|---|
| 1 | ROUNDUP ULTRA ® 3 SL | 0.84 (0.75) |
| 2 | ROUNDUP ULTRA ® 3 SL + ASSURE II ® 0.88 E | 0.84 (0.75) + 0.019 (0.017) |
| 3 | ROUNDUP ULTRA ® 3 SL + ASSURE II ® 0.88 E | 0.84 (0.75) + 0.028 (0.025) |
| 4 | ROUNDUP ULTRA ® 3 SL + ASSURE II ® 0.88 E | 0.84 (0.75) + 0.038 (0.034) |
| 5 | ASSURE II ® 0.88 E + NIS | 0.038 (0.034) + 0.125% V/V |
| 6 | POAST PLUS ® 1 E + DASH HC ® + UAN | 0.158 (0.141) + 1.17 L/ha (1 pt/ac) + 4.68 L/ha (4 pt/ac) |
| 7 | FUSILADE DX ® 2 E + NIS | 0.105 (0.094) + 0.25% V/V |
| 8 | SELECT ® 2 EC + COC + UAN | 0.071 (0.063) + 1.17 L/ha (1 pt/ac) + 4.68 L/ha (4 pt/ac) |

The active ingredient in ROUNDUP ULTRA® is glyphosate. The active ingredient in ASSURE II® is quizalofop, whereas the active ingredient in FUSILADE DX® is fluazifop. Sedthoxydim is the active ingredient in POAST PLUS®, and in SELECT® the active ingredient is cledthodim. All of the non-glyphosate herbicides used in this example are ACCase inhibitors. NIS is a non-ionic surfactant, comprising at least 80% active ingredient which is a mixture of polyoxkyethylated aliphatic alcohols, and free fatty acids or fatty acid esters. UAN is urea/ammonium nitrate fertilizer (28% nitrogen liquid). COC is an agricultural grade crop oil concentrate, which is a mixture of phytobland oils and surfactant, and DASH® is a surfactant (99%) produced specifically for use with POAST PLUS®.

The effectiveness of each mixture was tested by application at three different stages of corn growth: at 15–25 cm (6–10 in.), at 30–35 cm (12–14 in.), and at 40–50 cm (16–20 in.). Water at 93–187 L/ha (10–20 gal/ac) was used to make spray solutions. The percentage of control of each of the four tested corn lines by each of the above mixtures is given in Tables 2–4.

TABLE 2

| Treatment | "Natalie" (GT) | "Absurd" (BT) | 7800 (SR) | non-herbicide |
|---|---|---|---|---|
| 1 | 13 | 98 | 96 | 100 |
| 2 | 92 | 98 | 99 | 100 |
| 3 | 91 | 99 | 100 | 100 |
| 4 | 100 | 100 | 100 | 100 |
| 5 | 98 | 100 | 11 | 100 |
| 6 | 100 | 100 | 12 | 100 |
| 7 | 96 | 97 | 4 | 100 |
| 8 | 99 | 100 | 69 | 100 |

Percentage of control of corn lines by herbicide mixtures listed in Table 1 applied at corn heights of 15–25 cm (6–10 in.). Plots were scored at 28–38 days after treatment. Tabulated scores are the average over three locations. GT, glyphosate tolerant; BT, expressing a *Bacillus thuringiensis* insecticidal crystal protein and a poorly-expressed glyphosate tolerance marker gene, and exhibits tolerance to ROUNDUP ® only when treated at or before the 4 leaf stage or when the plants are 15 cm (6 in) or less; SR, sethoxydim resistant. All treatments are as given in Table 1.

TABLE 3

| Treatment | "Natalie" (GT) | "Absurd" (BT) | 7800 (SR) | non-herbicide |
|---|---|---|---|---|
| 1 | 3 | 100 | 100 | 100 |
| 2 | 51 | 99 | 100 | 100 |
| 3 | 63 | 100 | 100 | 100 |
| 4 | 71 | 100 | 100 | 100 |
| 5 | 88§ | 96 | 12 | 97§ |
| 6 | 93 | 95 | 11 | 94 |
| 7 | 97 | 97 | 11 | 98 |
| 8 | 95 | 93 | 40 | 96 |

Percentage of control of corn lines by herbicide mixtures listed in Table 1 applied at corn heights of 30–35 cm (12–14 in.). Plots were scored at 28–38 days after treatment. Tabulated scores are the average over four locations, except scores indicated by "§" are the average over three locations. GT, glyphosate tolerant; BT, expressing a *Bacillus thuringiensis* insecticidal crystal protein and a poorly-expressed glyphosate tolerance marker gene, and exhibits tolerance to ROUNDUP ® only when treated at or before the 4 leaf stage or when the plants are 15 cm (6 in) or less; SR, sethoxydim resistant. All treatments are as given in Table 1.

TABLE 4

| Treatment | "Natalie" (GT) | "Absurd" (BT) | 7800 (SR) | non-herbicide |
|---|---|---|---|---|
| 1 | 12 | 99 | 100 | 99 |
| 2 | 64 | 99 | 99 | 99 |
| 3 | 70 | 99 | 99 | 97 |
| 4 | 83 | 99 | 100 | 96 |
| 5 | 86 | 97 | 16 | 94 |
| 6 | 78 | 86 | 15 | 81 |
| 7 | 94 | 94 | 13 | 94 |
| 8 | 89 | 90 | 58 | 92 |

Percentage of control of corn lines by herbicide mixtures listed in Table 1 applied at corn heights of 40–50 cm (16–20 in.). Plots were scored at 28–38 days after treatment. Tabulated scores are the average over four locations. GT, glyphosate tolerant; BT, expressing a *Bacillus thuringiensis* insecticidal crystal protein and a poorly-expressed glyphosate tolerance marker gene, and exhibits tolerance to # ROUNDUP ® only when treated at or before the 4 leaf stage or when the plants are 15 cm (6 in) or less; SR, sethoxydim resistant. All treatments are as given in Table 1.

The results in Tables 2–4 demonstrate that mixtures of ROUNDUP ULTRA® and ASSURE II® (Treatments 2–4) may provide at least 50% control of glyphosate-tolerant corn, and if applied when corn is at a height of 15–20 cm (6–10 in.), may provide over 90% control of glyphosate-tolerant corn. Further, the extent of injury by any of the above mixtures to glyphosate-tolerant soybean was negligible, and no antagonism between ROUNDUP ULTRA® and ASSURE II® in control of grasses and broadleaf weeds was seen. However, SELECT® gave better control of SR corn than did ASSURE II®.

EXAMPLE 2

Tests were conducted at seven sites in the Midwestern U.S. At each site, replicated plots of glyphosate-tolerant soybean were planted, with the tested corn lines planted in multiple rows perpendicular to the soybean rows. Four corn lines were tested. One, "Natalie," was the glyphosate-tolerant corn used in Example 1. The second, "Natalie×SR," was a cross of Cargill 7900 (sethoxydim tolerant) and "Natalie." The final two were a sethoxydim tolerant corn line Asgrow RX620SR) and a non-herbicide-tolerant corn line.

Ten mixtures were used, as listed in Table 5:

TABLE 5

Herbicide formulations and rates of applications

| Treatment | Herbicides | Rate of application |
|---|---|---|
| 1 | ROUNDUP ULTRA ® 3 SL | 0.84 kg AE/ba (0.75 lbs. AE/ac) |
| 2 | ROUNDUP ULTRA ® 3 SL + FUSILADE DX ® 2 EC | 0.84 kg AE/ha (0.75 lbs. AE/ac) + 0.105 kg AI/ha (0.094 lbs. AI/ac) |
| 3 | ROUNDUP ULTRA ® 3 SL + FUSILADE DX ® 2 EC + NIS AD | 0.84 kg AE/ha (0.75 lbs. AE/ac) + 0.105 kg AI/ha (0.094 lbs. AI/ac) + 0.25% v/v |
| 4 | ROUNDUP ULTRA ® 3 SL + SELECT ® 2 EC | 0.84 kg AE/ha (0.75 lbs. AE/ac) + 0.041 kg AI/ha (0.036 lbs. AI/ac) |
| 5 | ROUNDUP ULTRA ® 3 SL + SELECT ® 2 EC | 0.84 kg AE/ha (0.75 lbs. AE/ac) + 0.071 kg AI/ha (0.063 lbs. AI/ac) |

TABLE 5-continued

Herbicide formulations and rates of applications

| Treatment | Herbicides | Rate of application |
|---|---|---|
| 6 | ROUNDUP ULTRA ® 3 SL + SELECT ® 2 EC | 0.84 kg AE/ha (0.75 lbs. AE/ac) + 0.105 kg AI/ha (0.094 lbs. AI/ac) |
| 7 | ROUNDUP ULTRA ® 3 SL + SELECT ® 2 EC + 100 AD + UAN | 0.84 kg AE/ha (0.75 lbs. AE/ac) + 0.105 kg AI/ha (0.094 lbs. AI/ac) + 1.17 l/ha (0.5 qt/ac) + 4.68 l/ha (2 qt/ac) |
| 8 | ROUNDUP ULTRA ® 3 SL + ASSURE II ® 0.88 EC | 0.84 kg AE/ha (0.75 lbs. AE/ac) + 0.038 kg AI/ha (0.034 lbs. AI/ac) |
| 9 | ROUNDUP ULTRA ® 3 SL + POAST PLUS ® 1 EC | 0.84 kg AE/ha (0.75 lbs. AE/ac) + 0.158 kg/AI/ha (0.141 lbs. AI/ac) |
| 10 | ROUNDUP ULTRA ® 3 SL + RAPTOR ® 1 SL | 0.84 kg AE/ha (0.75 lbs. AE/ac) + 0.027 kg AI/ha (0.024 lbs. AI/ac) |

The generic names for the herbicides used were given in Example 1 except for RAPTOR® (imazamox). Unlike the other herbicides tested, imazamox is an AHAS inhibitor. All applications were made at corn heights of 30–35 cm (12–14 in.), and weed control evaluations were made twice, 12–17 and 27–35 days after treatment. The percentage of control of each corn line by each mixture was determined, and the averages over the seven trial sites are given in Table 6.

provide effective control of glyphosate-susceptible weeds and glyphosate-tolerant corn in a crop of glyphosate-tolerant soybean.

EXAMPLE 3

Tests were conducted at eight sites in the Southern and Midwestern U.S. At each site, replicated plots of glyphosate-tolerant soybean were planted, with the tested corn lines

TABLE 6

Percentage of control of corn lines by the herbicide mixtures of Table 5. Abbreviations: GT, glyphosate tolerant; GT/SR, glyphosate tolerant and sethoxydim tolerant; SR, sethoxydim tolerant; DAT, days after treatment. All rates of ROUNDUP ULTRA ® application were 0.84 kg AE/ha (0.75 lbs. AE/ac); all rates of other herbicides are as given in Table 5, except for two ROUNDUP ULTRA ® + RAPTOR ® trials (Treatment 10), one at 0.045 kg AI/ha (0.04 lbs. AI/ac) RAPTOR ®, the other at 0.040 kg AI/ha (0.036 lbs. M/ac) RAPTOR ®.

| | "Natalie" (GT) | | "Natalie x SR" (GT/SR) | | "Cargill 7900" (SR) | | non-herbicide tolerant | |
|---|---|---|---|---|---|---|---|---|
| Treatment | 12–17 DAT | 27–35 DAT | 12–17 DAT | 27–35 DAT | 12–17 DAT | 27–35 DAT | 12–17 DAT | 27–35 DAT |
| 1 | 5 | 2 | 35 | 33 | 100 | 100 | 100 | 100 |
| 2 | 97 | 99 | 65 | 59 | 100 | 100 | 100 | 100 |
| 3 | 95 | 99 | 63 | 54 | 99 | 100 | 100 | 100 |
| 4 | 85 | 76 | 56 | 45 | 100 | 100 | 100 | 100 |
| 5 | 91 | 88 | 73 | 67 | 100 | 100 | 100 | 100 |
| 6 | 94 | 93 | 77 | 76 | 100 | 100 | 100 | 100 |
| 7 | 98 | 99 | 91 | 93 | 100 | 100 | 99 | 100 |
| 8 | 100 | 100 | 55 | 50 | 100 | 100 | 100 | 100 |
| 9 | 87 | 83 | 46 | 40 | 99 | 100 | 100 | 100 |
| 10 | 94 | 100 | 95 | 100 | 100 | 100 | 100 | 100 |

The above table indicates that mixtures of ROUNDUP ULTRA® with ACCase inhibitors or AHAS inhibitors can provide 85% or greater control of glyphosate tolerant corn. On corn expressing genes for both glyphosate tolerance and sethoxydim tolerance, mixtures of ROUNDUP ULTRA® with certain ACCase inhibitors, namely SELECT®, or AHAS inhibitors can provide 90% or better control, as opposed to only about 30% control for ROUNDUP ULTRA® alone. Further, no antagonism between ROUNDUP ULTRA® and any other herbicide tested was observed in the control of the broadleaf weed species velvetleaf (*Abutilon theophrasti*), sicklepod (*Cassia obtusifolia*), redroot pigweed (*Amaranthus retroflexus*), common lambsquarter (*Chenopodium album*), and common waterhemp (*Amaranthus rudis*). Soybean injury measured as a percentage of growth reduction was found to be in the range of 0–3% for all mixtures. In summary, mixtures of glyphosate with an ACCase-inhibitor or an AHAS-inhibitor planted in multiple rows perpendicular to the soybean rows. Two corn lines were tested. One, "RR F-2," was the $F_2$ generation of a glyphosate-tolerant corn line. The second, "RR×SR," was a cross of a sethoxydim-tolerant corn line and a glyphosate-tolerant corn line. The $F_2$ generations were a segregating population of the original corn hybrids and were representative of a volunteer corn population one would expect in a crop grown for commercial purposes. This is an effective method for testing volunteer populations. The safety of the mixtures was also tested by measuring growth reduction of glyphosate-tolerant soybeans.

The generic names for the herbicides used were given in Example 2. All applications were made at corn heights of 30–45 cm (12–18 in.), and weed control evaluations were made at 24–30 days after treatment. The percentage of control of each corn line by each mixture was determined, and the mixtures and the averages for each mixture over the eight trial sites are given in Table 7. Also provided by Table 7 is the consistency of the control of each corn line (defined as the number of locations at which control was greater than 90%, divided by the total number of locations), as well as a measure of the consistency of safety to the soybeans (the number of locations at which soybean growth reduction was greater than 5%, divided by the total number of locations).

TABLE 7

Percentage of control of corn lines by herbicide mixtures
Abbreviations: Tr. No., treatment number; GLXMA, glyphosate tolerant soybean; RR F-2 corn, volunteer glyphosate tolerant corn; RR X SR, cross pollinated volunteers of glyphosate tolerant and sethoxydim tolerant corn; GR %, percentage of growth reduction; MON 77683, a premixture of glyphosate and quizalofop.

| Tr. No. | Product | Rate lb ae or ai/A | GLXMA GR % | >5% GR[1] | RR F-2 corn Control | Consistency[2] | RR X SR corn Control | Consistency |
|---|---|---|---|---|---|---|---|---|
| 1. | ROUNDUP ULTRA ® | 0.75 | 0.8 | 0/7 | 13 | 0/8 | 32 | 0/7 |
| 2. | ROUNDUP ULTRA ® | 0.75 | 1.8 | 1/7 | 99 | 8/8 | 59 | 0/8 |
|  | FUSILADE DX ® | 0.094 | | | | | | |
| 3. | ROUNDUP ULTRA ® | 0.75 | 1.9 | 1/7 | 100 | 8/8 | 75 | 2/8 |
|  | FUSILADE DX ® | 0.094 | | | | | | |
|  | NIS | 0.25% v/v | | | | | | |
| 4. | ROUNDUP ULTRA ® | 0.75 | 1.3 | 1/7 | 97 | 7/8 | 73 | 2/8 |
|  | SELECT ® | 0.063 | | | | | | |
| 5. | ROUNDUP ULTRA ® | 0.75 | 1.3 | 1/7 | 100 | 8/8 | 84 | 5/8 |
|  | SELECT ® | 0.094 | | | | | | |
| 6. | ROUNDUP ULTRA ® | 0.75 | 1.3 | 1/7 | 99 | 8/8 | 91 | 5/8 |
|  | SELECT ® | 0.063 | | | | | | |
|  | Crop oil conc. | 0.5 qt/A | | | | | | |
|  | UAN 28% | 2 qt/A | | | | | | |
| 7. | ROUNDUP ULTRA ® | 0.75 | 1.5 | 2/7 | 100 | 8/8 | 95 | 6/8 |
|  | SELECT ® | 0.063 | | | | | | |
|  | Crop oil conc. | 0.5 qt/A | | | | | | |
|  | UAN 28% | 2 qt/A | | | | | | |
| 8. | ROUNDUP ULTRA ® | 0.75 | 1.0 | 1/7 | 86 | 4/8 | 40 | 0/8 |
|  | ASSURE II ® | 0.014 | | | | | | |
| 9. | ROUNDUP ULTRA ® | 0.75 | 1.9 | 2/7 | 99 | 8/8 | 51 | 1/8 |
|  | ASSURE II ® | 0.024 | | | | | | |
| 10. | ROUNDUP ULTRA ® | 0.75 | 1.0 | 1/7 | 98 | 8/8 | 49 | 0/8 |
|  | ASSURE II ® | 0.034 | | | | | | |
| 11. | ROUNDUP ULTRA ® | 0.75 | 1.3 | 1/7 | 96 | 8/8 | 45 | 0/8 |
|  | POAST PLUS ® | 0.141 | | | | | | |
| 12. | ROUNDUP ULTRA ® | 0.75 | 2.7 | 2/7 | 85 | 6/8 | 91 | 6/8 |
|  | RAPTOR ® | 0.016 | | | | | | |
| 13. | ROUNDUP ULTRA ® | 0.75 | 4.7 | 2/7 | 93 | 6/8 | 96 | 7/8 |
|  | RAPTOR ® | 0.024 | | | | | | |
| 14. | ROUNDUP ULTRA ® | 0.75 | 4.8 | 2/7 | 96 | 7/8 | 97 | 7/8 |
|  | RAPTOR ® | 0.032 | | | | | | |
| 15. | TOUCHDOWN 5 ® | 0.94 | 1.6 | 1/7 | 25 | 0/8 | 45 | 0/7 |
| 16. | TOUCHDOWN 5 ® | 0.94 | 2.3 | 2/7 | 99 | 8/8 | 63 | 0/8 |
|  | FUSILADE DX ® | 0.094 | | | | | | |
|  | NIS | 0.25% v/v | | | | | | |
| 17. | TOUCHDOWN 5 ® | 0.94 | 1.4 | 0/7 | 99 | 7/7 | 63 | 1/8 |
|  | FUSION ® | 0.125 | | | | | | |
|  | NIS | 0.25% v/v | | | | | | |

TABLE 7-continued

Percentage of control of corn lines by herbicide mixtures
Abbreviations: Tr. No., treatment number; GLXMA, glyphosate tolerant soybean; RR F-2 corn, volunteer glyphosate tolerant corn; RR X SR, cross pollinated volunteers of glyphosate tolerant and sethoxydim tolerant corn; GR %, percentage of growth reduction; MON 77683, a premixture of glyphosate and quizalofop.

| Tr. No. | Product | Rate lb ae or ai/A | GLXMA GR % | >5% GR[1] | RR F-2 corn Control | Consistency[2] | RR X SR corn Control | Consistency |
|---|---|---|---|---|---|---|---|---|
| 18. | MON 77683[3] | 1.043 | 2.1 | 1/6 | 98 | 6/7 | 55 | 1/7 |
| 19. | M0N 77683 NIS | 1.043 0.125% v/v | 3.5 | 3/6 | 99 | 7/7 | 50 | 0/7 |

[1]Number of locations with ≧5% GR per total number of locations.
[2]Number of locations with ≧90% control per total number of locations.
[3]MON 77683: Premix formulation of Glyphosate + Commercial ASSURE II ® in 22:1 ratio.

Most products were not injurious (growth reduction<about 5%) to glyphosate-tolerant soybeans, with the exception of treatments no. 13 and 14, which contained RAPTOR®.

All graminicide mixtures gave over 90% control of glyphosate tolerant volunteer corn, except the lowest rate of ASSURE II® (0.014 lb ai/A) and RAPTOR® (0.016 lb ai/A). Although higher rates of some graminicides or addition of additives in the tank-mix did not increase the percentage control, they improved the consistency of glyphosate-tolerant volunteer corn control (e.g SELECT® Treatment Nos. 5–7).

Only RAPTOR® (0.016 to 0.032 lb ai/A) and SELECT® (0.063 to 0.094 lb ai/A) provided commercial control of volunteer corn that were tolerant to both glyphosate and sethoxydim (RR×SR cross). SELECT® however, needed additives for more consistent control.

A number of other observations were made that are not shown in Table 7. First, control of a variety of weeds was studied. The weeds were foxtail, barnyardgrass, broadleaf signalgrass, pigweed, lambsquarter, velvetleaf, morningglory, cocklebur, common purslane, common ragweed, prickly sida, and ladysthumb. No antagonism of weed control was seen with tank mixes compared to ROUNDUP ULTRA® alone. In addition, a number of cases of weed control synergy occurred. At a site in the Southern United States, tankmixing label rates of ASSURE II®, SELECT®, RAPTOR®, and FUSILADE® with ROUNDUP ULTRA® improved the control of broadleaf signalgrass over ROUNDUP ULTRA® alone (1 qt/A). At a site in the Midwestern United States, ROUNDUP ULTRA®, plus RAPTOR® and AMS (spray grade ammonium sulfate) provided additional broadleaf control of ladysthumb and hedge bindweed over ROUNDUP ULTRA® alone (1 qt/A).

EXAMPLE 4

Tank mixtures of ROUNDUP ULTRA® and graminicides were tested to identify potential antagonism/synergism associated with volunteer wheat burndown. Field experiments were conducted at a site in the Midwestern United States. The products used in the mixtures are as given in Example 2. Observations on volunteer wheat control were made at 10, 14, 16, and 19 days after the initial treatment. Data are presented in Table 8.

TABLE 8

Control of volunteer wheat. Abbreviations used: DAT, days after treatment. Each value is a mean of 4 replications.

| Tr. No. | Product | Rate lb ae or ai/A | Volunteer wheat (% control) | | | |
|---|---|---|---|---|---|---|
| | | | 10 DAT | 14 DAT | 16 DAT | 19 DAT |
| 1. | ROUNDUP ULTRA ® | 0.75 | 16 | 53 | 90 | 98 |
| 2. | ROUNDUP ULTRA ® FUSILADE DX ® | 0.75 0.094 | 21 | 46 | 79 | 95 |
| 3. | ROUNDUP ULTRA ® FUSILADE DX ® NIS | 0.75 0.094 0.25% v/v | 24 | 48 | 91 | 92 |
| 4. | ROUNDUP ULTRA ® SELECT ® | 0.75 0.063 | 19 | 54 | 88 | 99 |
| 5. | ROUNDUP ULTRA ® SELECT ® | 0.75 0.094 | 20 | 48 | 94 | 94 |
| 6. | ROUNDUP ULTRA ® SELECT ® Crop oil conc. UAN 28% | 0.75 0.063 0.5 qt/A 2 qt/A | 28 | 60 | 92 | 98 |
| 7. | ROUNDUP ULTRA ® SELECT ® Crop oil conc. UAN 28% | 0.75 0.063 0.5 qt/A 2 qt/A | 18 | 60 | 95 | 93 |
| 8. | ROUNDUP ULTRA ® ASSURE II ® | 0.75 0.014 | 21 | 40 | 90 | 90 |
| 9. | ROUNDUP ULTRA ® ASSURE II ® | 0.75 0.024 | 21 | 51 | 90 | 95 |
| 10. | ROUNDUP ULTRA ® ASSURE II ® | 0.75 0.034 | 21 | 56 | 92 | 99 |
| 11. | ROUNDUP ULTRA ® POAST PLUS ® | 0.75 0.141 | 19 | 53 | 91 | 99 |
| 12. | ROUNDUP ULTRA ® RAPTOR ® | 0.75 0.016 | 18 | 48 | 96 | 98 |
| 13. | ROUNDUP ULTRA ® RAPTOR ® | 0.75 0.024 | 24 | 55 | 96 | 98 |

TABLE 8-continued

Control of volunteer wheat. Abbreviations used: DAT, days after treatment. Each value is a mean of 4 replications.

| Tr. No. | Product | Rate lb ae or ai/A | Volunteer wheat (% control) | | | |
|---|---|---|---|---|---|---|
| | | | 10 DAT | 14 DAT | 16 DAT | 19 DAT |
| 14. | ROUNDUP ULTRA ® RAPTOR ® | 0.75 0.032 | 18 | 46 | 92 | 93 |
| 15. | TOUCHDOWN 5 ® | 0.94 | 23 | 50 | 99 | 98 |
| 16. | TOUCHDOWN 5 ® FUSILADE DX ® NIS | 0.94 0.094 0.25% v/v | 15 | 46 | 81 | 95 |
| 17. | TOUCHDOWN 5 ® FUSION ® NIS | 0.94 0.125 0.25% v/v | 14 | 39 | 70 | 80 |

None of the graminicides in the tank-mix with ROUNDUP ULTRA® (0.75 lb ae/A) produced antagonism. Compare treatment no. 1 with treatment nos. 2–14.

EXAMPLE 5

Mixtures of ROUNDUP ULTRA® and graminicides were tested in the control of tough grasses, defined as grass species which are generally held by one of ordinary skill in the art to be more highly resistant to herbicides than the average grass species. The species tested were quackgrass, johnsongrass, barnyardgrass, woollycup grass, and wheat.

The objectives were to determine the most beneficial tank-mix/premix ratio, and any additional benefit of the mixture in controlling tough grasses. Data were collected 13 and 20 days after spraying, and results are given in Tables 9 and 10.

TABLE 9

| Treatment | Rate | AGRRE | SORHA | TRZAW | ECHCG | ERBVI |
|---|---|---|---|---|---|---|
| ROUNDUP ULTRA ® alone | 0.375 lb/A | 40 | 30 | 50 | 77 | 73 |
| | 0.75 lb/A | 98 | 100 | 92 | 92 | 93 |
| ROUNDUP ULTRA ® + SELECT ® | 0 lb/A 0.094 lb/A | 8 | 23 | 17 | 90 | 45 |
| ASSURE ® | 0.034 lb/A | 22 | 68 | 58 | 97 | 57 |
| RAPTOR ® | 0.032 lb/A | 5 | 17 | 7 | 7 | 7 |
| ROUNDUP ULTRA ® + SELECT ® | 0.375 lb/A 0.094 lb/A | 28 | 67 | 80 | 95 | 83 |
| ASSURE ® | 0.034 lb/A | 38 | 77 | 72 | 98 | 90 |
| RAPTOR ® | 0.032 lb/A | 60 | 85 | 82 | 97 | 88 |
| ROUNDUP ULTRA ® + SELECT ® | 0.75 lb/A 0.094 lb/A | 95 | 97 | 95 | 100 | 100 |

TABLE 9-continued

| Treatment | Rate | AGRRE | SORHA | TRZAW | ECHCG | ERBVI |
|---|---|---|---|---|---|---|
| ASSURE ® | 0.034 lb/A | 83 | 80 | 90 | 100 | 100 |
| RAPTOR ® | 0.032 lb/A | 85 | 88 | 95 | 93 | 92 |

Effect of graminicides at labeled rates alone or in the tank-mix with ROUNDUP ULTRA ® on tough grasses at 13 DAT. Abbreviations used: AGRRE (*Agropyron repens*; quackgrass), SORHA (*Sorghum halepense*; johnsongrass), TRZAW (*Triticum aestivum*; wheat), ECHCG (*Echinochloa crus-galli*; barnyardgrass), ERBVI (*Eriochloa villosa*; woolly cupgrass).

TABLE 10

Effect of graminicides at labeled rates alone or in tank-mix with ROUNDUP ULTRA ® on tough grasses at 20 DAT. Abbreviations used are as given in the heading for Table 9.

| Treatment. | Rate | AGRRE | SORHA | TRZAW | ECHCG | ERBVI |
|---|---|---|---|---|---|---|
| ROUNDUP ULTRA ® alone | 0.375 lb/A | 57 | 67 | 80 | 94 | 84 |
| | 0.75 lb/A | 100 | 100 | 97 | 96 | 98 |
| ROUNDUP ULTRA ® + SELECT ® | 0 lb/A 0.094 lb/A | 13 | 35 | 22 | 100 | 62 |
| ASSURE ® | 0.034 lb/A | 50 | 100 | 93 | 100 | 90 |
| RAPTOR ® | 0.032 lb/A | 7 | 23 | 15 | 12 | 23 |
| ROUNDUP ULTRA ®+ SELECT ® | 0.375 lb/A 0.094 lb/A | 68 | 95 | 99 | 97 | 100 |
| ASSURE ® | 0.034 lb/A | 78 | 98 | 100 | 99 | 98 |
| RAPTOR ® | 0.032 lb/A | 79 | 98 | 97 | 98 | 97 |
| ROUNDUP ULTRA ® + SELECT ® | 0.75 lb/A 0.094 lb/A | 97 | 98 | 100 | 98 | 100 |
| ASSURE ® | 0.034 lb/A | 98 | 97 | 99 | 100 | 100 |
| RAPTOR ® | 0.032 lb/A | 100 | 100 | 100 | 99 | 99 |

Graminicides alone were not effective in controlling test grass species, with the exception that ASSURE® and SELECT® at labeled rates gave acceptable control (90% or more) of barnyardograss at 13 DAT (Table 9). By 20 DAT, ASSURE® proved to be a better stand alone product than RAPTOR® and SELECT® (Table 10). However, none of these products controlled quackgrass.

Figure 1:
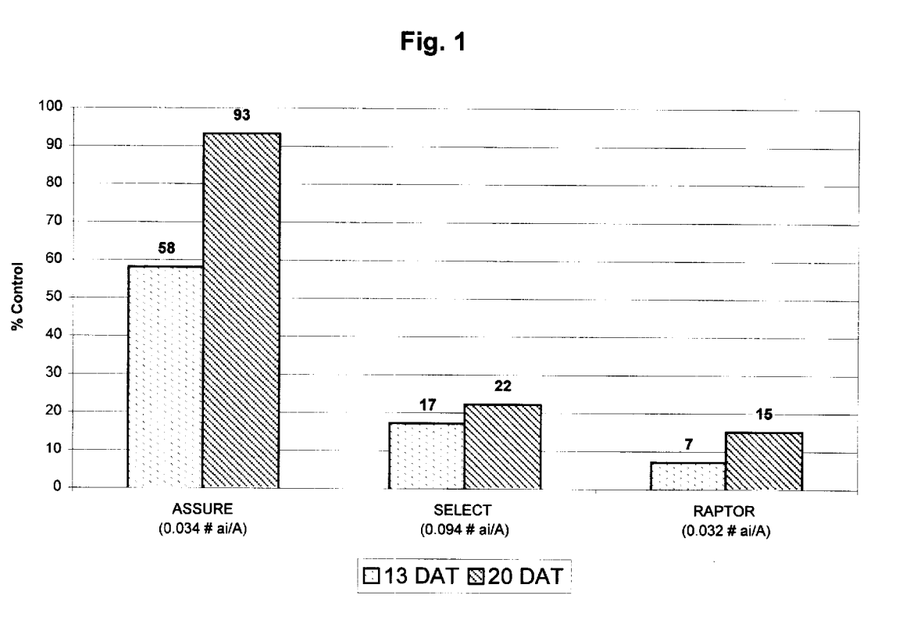
FIG. 1 shows the effect of three graminicides on volunteer wheat.

ASSURE II® was the only product which gave commercial level of control of volunteer wheat by 20 DAT. Both RAPTOR® and SELECT® were not active on volunteer wheat (FIG. 1).

ROUNDUP ULTRA® alone at 0.5 qt/A was not commercially acceptable (i.e. less than 90% control). However, 1 qt/A gave over 90% control of all test weed species.

Control of most grasses improved with 0.5 qt ROUNDUP ULTRA® when tankmixed with graminicides. This indicates a synergistic effect at this level of ROUNDUP ULTRA®.

ROUNDUP ULTRA® alone at 1.0 qt/A rate was as effective as ROUNDUP ULTRA® and graminicide tank mixtures (at all rates of graminicide in general, including those not shown, with few exceptions). This indicates that no antagonism occurs between the graminicides and ROUNDUP ULTRA®.

EXAMPLE 6

Experiments were performed to evaluate whether additives were needed to improve the efficacy of mixtures of ROUNDUP ULTRA® and graminicide. Tank-mixes of ROUNDUP ULTRA® and graminicide were prepared as listed below, and tested against three volunteer herbicide-tolerant corns (HTCs), rice, and wheat. ROUNDUP ULTRA® alone (1 qt/A) was used as a control. Formulations tested and results are provided below in Tables 11 and 12.

TABLE 11

Effect of additives in ROUNDUP ULTRA ® and graminicide mixtures on volunteer corn, wheat, and rice control 13 DAT. Abbreviations used: ZEAPT, sethoxydim-tolerant corn; ZEAMI, imidazolinone-tolerant corn; ZEAMG, glyphosate-tolerant corn; ORYSI, rice; TRZAW, wheat.

| ROUNDUP ULTRA ® | Rate (lb/A) | ZEAPT NO | ZEAPT YES | ORYSI NO | ORYSI YES | ZEAMI NO | ZEAMI YES | TRZAW NO | TRZAW YES | ZEAMG NO | ZEAMG YES |
|---|---|---|---|---|---|---|---|---|---|---|---|
| ROUNDUP ULTRA ® + | 0.75 | 68 | | 70 | | 73 | | 60 | | 0 | |
| SELECT ® | 0.031 | 97 | 87 | 80 | 100 | 100 | 88 | 97 | 92 | 77 | 95 |
|  | 0.063 | 78 | 73 | 93 | 98 | 82 | 87 | 87 | 95 | 82 | 85 |
|  | 0.094 | 62 | 93 | 93 | 100 | 80 | 88 | 90 | 97 | 85 | 98 |
| ASSURE II ® | 0.011 | 85 | 80 | 97 | 100 | 98 | 100 | 100 | 95 | 100 | 97 |
|  | 0.023 | 58 | 78 | 87 | 97 | 87 | 93 | 97 | 88 | 100 | 97 |
|  | 0.034 | 92 | 85 | 100 | 98 | 95 | 97 | 100 | 98 | 100 | 95 |
| POAST PLUS ® | 0.047 | 80 | 87 | 98 | 82 | 90 | 85 | 83 | 98 | 52 | 33 |
|  | 0.094 | 63 | 83 | 95 | 92 | 92 | 88 | 90 | 88 | 38 | 57 |
|  | 0.141 | 60 | 78 | 93 | 100 | 95 | 72 | 98 | 78 | 72 | 60 |
| RAPTOR ® | 0.011 | 93 | 92 | 87 | 98 | 90 | 93 | 90 | 98 | 12 | 13 |
|  | 0.021 | 73 | 88 | 90 | 97 | 85 | 95 | 80 | 90 | 7 | 12 |
|  | 0.032 | 83 | 80 | 93 | 67 | 92 | 85 | 68 | 92 | 13 | 30 |
| FUSILADE DX ® | 0.031 | 80 | 60 | 92 | 88 | 82 | 77 | 83 | 87 | 57 | 80 |
|  | 0.063 | 75 | 88 | 82 | 92 | 77 | 87 | 78 | 93 | 85 | 90 |
|  | 0.094 | 67 | 70 | 95 | 92 | 72 | 77 | 88 | 83 | 83 | 73 |

NOTE: "YES" = with additives, "NO" = without additives, where the additives used are:
1. with SELECT ®: Crop Oil Conc. at 0.5 qt/A + UAN 28% at 2 qt/A
2. with ASSURE II ®: NIS at 0.125%
3. with POAST PLUS ®: COC at 1 qt/A + AMS at 2.5 lb/A
4. with RAPTOR ®: COC at 1 qt/A + AMS at 2.5 lb/A
5. with FUSILADE DX ®: NIS at 0.25%

TABLE 12

Effect of additives in ROUNDUP ULTRA ® and graminicide mixtures on volunteer corn, wheat, and rice control 20 DAT. Abbreviations used are as defined in the heading of Table 11.

| | Rate (lb/A) | ZEAPT NO | ZEAPT YES | ORYSI NO | ORYSI YES | ZEAMI NO | ZEAMI YES | TRZAW NO | TRZAW YES | ZEAMG (RR corn) NO | ZEAMG (RR corn) YES |
|---|---|---|---|---|---|---|---|---|---|---|---|
| ROUNDUP ULTRA ® + | 0.75 | 98 | | 83 | | 100 | | 95 | | 0 | |
| SELECT ® | 0.031 | 95 | 98 | 80 | 98 | 100 | 100 | 100 | 100 | 87 | 100 |
|  | 0.063 | 95 | 93 | 98 | 100 | 100 | 100 | 93 | 100 | 100 | 98 |
|  | 0.094 | 100 | 100 | 100 | 100 | 100 | 100 | 100 | 100 | 100 | 100 |
| ASSURE II ® | 0.011 | 100 | 100 | 98 | 100 | 100 | 100 | 100 | 100 | 100 | 100 |
|  | 0.023 | 97 | 100 | 97 | 98 | 100 | 100 | 100 | 100 | 100 | 100 |
|  | 0.034 | 100 | 98 | 100 | 100 | 100 | 100 | 100 | 100 | 100 | 100 |
| POAST PLUS ® | 0.047 | 100 | 98 | 100 | 93 | 100 | 100 | 100 | 100 | 78 | 65 |
|  | 0.094 | 97 | 99 | 98 | 96 | 100 | 100 | 100 | 100 | 90 | 88 |
|  | 0.141 | 100 | 95 | 97 | 100 | 100 | 100 | 100 | 100 | 95 | 100 |
| RAPTOR ® | 0.011 | 100 | 95 | 100 | 100 | 100 | 100 | 100 | 100 | 42 | 55 |
|  | 0.021 | 93 | 100 | 98 | 100 | 98 | 100 | 93 | 100 | 33 | 63 |
|  | 0.032 | 95 | 90 | 100 | 82 | 100 | 100 | 100 | 100 | 72 | 73 |
| FUSILADE | 0.031 | 100 | 95 | 98 | 98 | 100 | 100 | 100 | 100 | 97 | 97 |

TABLE 12-continued

Effect of additives in ROUNDUP ULTRA ® and graminicide mixtures on volunteer corn, wheat, and rice control 20 DAT. Abbreviations used are as defined in the heading of Table 11.

|  | Rate | ZEAPT | | ORYSI | | ZEAMI | | TRZAW | | ZEAMG (RR corn) | |
|---|---|---|---|---|---|---|---|---|---|---|---|
|  | (lb/A) | NO | YES | NO | YES | NO | YES | NO | YES | NO | YES |
| DX ® | 0.063 | 97 | 95 | 100 | 98 | 100 | 100 | 100 | 98 | 100 | 97 |
|  | 0.094 | 93 | 99 | 97 | 100 | 98 | 100 | 100 | 100 | 100 | 100 |

NOTE: "YES" = with additives, "NO" = without additives, where the additives used are:
1. with SELECT ®: Crop Oil Conc. at 0.5 qt/A + UAN 28% at 2 qt/A
2. with ASSURE II ®: NIS at 0.125%
3. with POAST PLUS ®: COC at 1 qt/A + AMS at 2.5 lb/A
4. with RAPTOR ®: COC at 1 qt/A + AMS at 2.5 lb/A
5. with FUSILADE DX ®: NIS at 0.25%

All graminicides tested at all rates (except in a few occasions) improved the control of all test species (three volunteer herbicide-tolerant corns, rice, and wheat) over ROUNDUP ULTRA® alone (1 qt/A) at 13 DAT (Table 11). But, by 20 DAT, there was no difference in control between ROUNDUP ULTRA® alone and tank-mix treatments except in rice and glyphosate-tolerant corn (Table 12). Graminicides in the tank-mix improved the control of rice (Tables 11 and 12).

Regarding SELECT®, additives improved control of rice and glyphosate-tolerant corn at the lowest rate of SELECT® (0.031 lb ai/A). At higher rates, additives gave no benefit (Table 12).

Regarding ASSURE II®, good control of all test species was observed with or without additives.

Regarding POAST PLUS®, poor control of glyphosate-tolerant corn and also sethoxydim-tolerant corn was seen at 13 DAT. Additives only improved control of sethoxydim-tolerant corn, but not glyphosate-tolerant corn (Table 11). Control improved by 20 DAT when the labeled rate of POAST PLUS®, 0.141 lb ai/A, was used in the mixture.

Regarding RAPTOR®, poor control of glyphosate-tolerant corn was seen either with or without additives. Typical symptoms of treatment with ALS-inhibitor herbicides were seen on glyphosate-tolerant corn, but plants were not completely killed even at 20 DAT.

Regarding FUSILADE DX®, it gave inconsistent control of sethoxydim-tolerant corn at 13 DAT. Additives provided synergism at lower rates, and possible antagonism at higher rates (Table 11). Additives showed no benefit at 20 DAT (Table 12).

In conclusion, tank mixtures of ROUNDUP ULTRA® and graminicides improved control of rice over ROUNDUP ULTRA® alone (1 qt/A). In all species tested, the effect of additives, if any, was more evident within the first two weeks (13 d) after treatment. After three weeks (20 d), the differences were negligible. Finally, additives did improve control of glyphosate-tolerant corn of mixtures comprising the lowest rate of SELECT®.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos.
3,799,758
3,927,080
3,956,370
3,969,398
4,147,719
4,654,429
5,310,667
5,312,910
5,463,175

Other references
Flint et al, *Weed Science* (1989), 37, 700–705
Lich Et AL., *Weed Science* (1997), 45, 12–21

What is claimed is:

1. An herbicidal mixture comprising a glyphosate herbicide and a non-glyphosate herbicide that is an ACCase inhibitor or an AHAS inhibitor, wherein said non-glyphosate herbicide is selected from the group consisting of quizalofop, clethodim, sethoxydim, imazamox, and fenoxaprop.

2. The herbicidal mixture of claim 1, wherein the non-glyphosate herbicide is quizalofop.

3. The herbicidal mixture of claim 1, wherein the non-glyphosate herbicide is clethodim.

4. The herbicidal mixture of claim 1, wherein the non-glyphosate herbicide is sethoxydim.

5. The herbicidal mixture of claim 1, wherein the non-glyphosate herbicide is imazamox.

6. The herbicidal mixture of claim 1, wherein the non-glyphosate herbicide is fenoxaprop.

7. A method for controlling glyphosate-susceptible weeds and a glyphosate-tolerant first plant species growing in a crop of a glyphosate-tolerant second plant species, comprising:

first applying a non-glyphosate herbicide to the crop of the glyphosate-tolerant second plant species, the non-glyphosate herbicide being toxic to the first plant species and non-toxic to the second plant species, at a rate of application sufficient to control the first plant species; and, second applying a glyphosate herbicide to the crop of the glyphosate-tolerant second plant species at a rate of application sufficient to control the glyphosate-susceptible weeds, wherein the first applying and the second applying steps can be performed in either order or simultaneously.

8. The method of claim 7, wherein the first plant species is glyphosate-tolerant corn, wheat, or rice, and the second plant species is glyphosate-tolerant soybean, canola, sugarbeet, or cotton.

9. The method of claim 8, wherein the non-glyphosate herbicide is fluazifop.

10. The method of claim 9, wherein the rate of application of the glyphosate herbicide is from about 0.42 to about 0.84 kg AE per ha, and the rate of application of the fluazifop is about 0.105 kg AI per ha.

11. The method of claim 8, wherein the non-glyphosate herbicide is quizalofop.

12. The method of claim 11, wherein the rate of application of the glyphosate herbicide is from about 0.42 to about 0.84 kg AE per ha, and the rate of application of the quizalofop is from about 0.019 kg AI per ha to about 0.076 kg AI per ha.

13. The method of claim 8, wherein the non-glyphosate herbicide is clethodim.

14. The method of claim 13, wherein the rate of application of the glyphosate herbicide is from about 0.42 to about 0.84 kg AE per ha, and the rate of application of the clethodim is from about 0.1 kg AI per ha to about 0.21 kg AI per ha.

15. The method of claim 8, wherein the non-glyphosate herbicide is sethoxydim.

16. The method of claim 15, wherein the rate of application of the glyphosate herbicide is from about 0.42 to about 0.84 kg AE per ha, and the rate of application of the sethoxydim is from about 0.158 to about 0.316 kg AI per ha.

17. The method of claim 8, wherein the non-glyphosate herbicide is imazamox.

18. The method of claim 17, wherein the rate of application of the glyphosate herbicide is from about 0.42 to about 0.84 kg AE per ha, and the rate of application of the imazamox is from about 0.027 to about 0.045 kg AI per ha.

19. The method of claim 8, wherein the non-glyphosate herbicide is fenoxaprop.

20. The method of claim 19, wherein the rate of application of the glyphosate herbicide is from about 0.42 to about 0.84 kg AE per ha, and the rate of application of the fenoxaprop is about 0.105 kg AI per ha.

21. The method of claim 7, further comprising preparing a mixture of the glyphosate herbicide and the non-glyphosate herbicide prior to the applying steps, and wherein the applying steps are performed simultaneously.

* * * * *

UNITED STATES PATENT AND TRADEMARK OFFICE
CERTIFICATE OF CORRECTION

PATENT NO. : 6,239,072 B1
DATED : May 29, 2001
INVENTOR(S) : Jerry L. Flint et al.

Page 1 of 1

It is certified that error appears in the above-identified patent and that said Letters Patent is hereby corrected as shown below:

Title page,
Item [54], Title, reads "TANK MIXTURES AND PREMIXTURES FOR WEED CONTROL PROGRAMS THAT INCLUDE POSTMERGENCE APPLICATIONS OF GLYPHOSATE PLUS GRAMINICIDES IN GLYPHOSATE TOLERANT SOYBEANS" and should read -- TANK MIXTURES AND PREMIXTURES FOR WEED CONTROL PROGRAMS THAT INCLUDE POSTEMERGENCE APPLICATIONS OF GLYPHOSATE PLUS GRAMINICIDES IN GLYPHOSATE TOLERANT SOYBEANS. --

Signed and Sealed this

Twenty-sixth Day of April, 2005

JON W. DUDAS
*Director of the United States Patent and Trademark Office*